(12) United States Patent
Trushin et al.

(10) Patent No.: US 6,584,342 B1
(45) Date of Patent: Jun. 24, 2003

(54) METHOD FOR DIAGNOSING PROLIFERATION REGIONS AND DEVICE FOR REALIZING THE SAME

(76) Inventors: Alexei I. Trushin, Russian Federation, 117335, Moscow, ul Profsoyuznaya, d. 38, k. 1, kv. 20 (RU); Alexandr V. Vinogradov, Russian Federation, 117335, Moscow, ul. Profsoyuznaya, d. 44, k. 5, kv. 7 (RU); Mikhail L. Stakhanov, Russian Federation, 105318, Moscow. ul. Scherbakovskaya, d. 26/30, kv. 127 (RU)

(*) Notice: Subject to any disclaimer, the term of this patent is extended or adjusted under 35 U.S.C. 154(b) by 0 days.

(21) Appl. No.: 09/869,645
(22) PCT Filed: Feb. 12, 1999
(86) PCT No.: PCT/RU99/00039
§ 371 (c)(1), (2), (4) Date: Jul. 2, 2001
(87) PCT Pub. No.: WO00/47112
PCT Pub. Date: Aug. 17, 2000

(51) Int. Cl.[7] .................................................. A61B 6/00
(52) U.S. Cl. ............................................................. 600/476
(58) Field of Search .................................. 600/476, 300, 600/407; 382/128; 128/633, 634, 665

(56) References Cited

U.S. PATENT DOCUMENTS

| | | | | |
|---|---|---|---|---|
| 4,930,516 A | * | 6/1990 | Alfano et al. | 600/477 |
| 5,419,323 A | * | 5/1995 | Kittrell et al. | 600/476 |
| 5,760,407 A | * | 6/1998 | Margosiak et al. | 250/461.1 |
| 5,998,597 A | * | 12/1999 | Fisher et al. | 128/898 |
| 6,083,485 A | * | 7/2000 | Licha et al. | 424/1.11 |
| 6,324,419 B1 | * | 11/2001 | Guzelsu et al. | 600/473 |
| 6,393,315 B1 | * | 5/2002 | Aprahamian et al. | 356/402 |

* cited by examiner

Primary Examiner—Teresa Walberg
Assistant Examiner—Daniel Robinson
(74) Attorney, Agent, or Firm—Notaro & Michalos P.C.

(57) ABSTRACT

Non-invasive, contract-free method for the diagnostics of the proliferation areas of biological tissue and their localization zones n vivo in a live organism on the basis of visualizing the fluorescence of endogenous porphyrins and a device for implementing this method. Tissue is irradiated with low intensity monochrome radiation in the wave length band of 630 to 645 nm and the fluorescent image is recorded within the band of 650 to 730 nm. Recording is carried out in one or several cycles, the brightness values of the corresponding points in the images are averaged for all recording cycles, the significant brightness range of the averaged image is established and broadened by way of re-calculation with regard to the entire dynamic range of the display device. A color reference image of the tissue and auxiliary images are recorded additionally at the excitation wave length and at the fluorescence wave length with illumination from the corresponding sources, and the fluorescent images of the natural proliferation areas of the same patient and a fluorescing test object are recorded. The device for implementing this method contains an additional laboratory premises lighting source.

9 Claims, 2 Drawing Sheets

METHOD FOR DIAGNOSING PROLIFERATION REGIONS AND DEVICE FOR REALIZING THE SAME

FIELD OF TECHNOLOGY

This invention relates to medicine and, more particularly, to contact-free clinical diagnostics of proliferation areas in biological tissues and their localisation areas in vivo in a live organism on the basis of endogenous porphyrin fluorescence.

PREVIOUS LEVEL OF TECHNOLOGY

Both the known and the proposed proliferation area diagnostics methods are based on the ability of porphyrins to be localised selectively in proliferating tissues (The Big Medical Encyclopaedia, RU, Moscow, Sovetskaya Entsiklopedia Publishers, 1983, Volume 20, Page 349)

The known proliferation area diagnostics methods in oncology are the introduction of exogenous porphyrins to a patient (Photodynamic Therapy and Fluorescent Diagnostics of Malignant Tumours with the Use of Photogem Preparation, V.I. Chissov et al., Khirurgiya (Surgery), No. 12, 1994, p. 3–6; Clinical Fluorescent Tumour Diagnostics with Photosensitinogen Photogem, V.I. Chisov et al. Khirurgia (Surgery), No. 5, 1995, p. 37–41; (see also references in those articles) or the introduction of the preparations that stimulate active generation of endogenous porphyrins in a patient's organism (Pharmacokinetic of Endogenous Porphyrins Induced by 5-Aminolevulinic Acid as Observed by Means of Laser Induced Fluorescence from Several Organs of Tumour-Bearing Mice, Ronald Sroka, Reinhold Baugartner, Wolfgang Beyer, Liebwin Gossner, Tarek Sassy, Susanne Stocker., BIOS'95, 4–10 February. 1995, SPIE Proc. Vol. 2387, pp. 22–29) and, after some time, sufficient for selective re-distribution of the introduced exogenous porphyrins in tissues or stimulation of the generation and re-distribution of endogenous porphyrins, consecutive irradiation of small segments of the surface of the tissue under examination with the wave length which falls into the porphyrin fluorescence excitation band, with the recording of the fluorescence band simultaneously to that.

The main disadvantage of these diagnostics methods is their invasiveness, that is, the need for the introduction to a patient of either exogenous porphyrins or the substances which stimulate active generation of endogenous porphyrins in the organism. Increase in the content of porphyrins in the organism results in all negative developments typical of porphyria, such as, porphyrin exchange disfunction, including significant increase in photosensitivity of the organism. In this connection the given methods cannot be used in primary diagnostic examination, particularly in case of public preventive monitoring of the population.

The disadvantages of the indicated diagnostics methods also include their low performance caused first of all by quite a long period of time required for the selective re-distribution of the introduced exogenous porphyrins in tissues or the stimulation of the generation and re-distribution of endogenous porphyrins. Besides, the indicated methods record fluorescence bands which implies consecutive analysis of the tissue under examination from one point to another. Apart from the optic properties of the tissue proper, the size of a point, that is the area of tissue being examined at a given time, is also determined by the apertures of the radiation which induces fluorescence and the optical fibres which receive the fluorescent response and the location of their front-sides in relation to the tissue under examination. This results in low spatial resolution and poor reproducibility of the measurement results for the given methods. If it is necessary to examine big areas of various organs, skin etc., the probability of "blanks", that is, the segments of the tissue under diagnostics that escape examination, is high. Besides, a disadvantage of the given methods is that it is difficult to document the location of proliferation areas and their localisation boundaries.

A known cancer identification method (Tumor detection in HpD-sensitized mice with fluorescence lifetime imaging, R. Cubeddu, G. Canti, A. Pifferi, P. Taroni, and G. Valentini, SPIE Proc. Vol, 2972, pp. 148–153) is the introduction of an exogenous derivative of hematoporphyrin and after some time, sufficient for its selective re-distribution in tissues, the exposure of the tissue under examination to short radiation pulses which induce fluorescence of the hematoporphyrin derivative with the wave length of 405 nm and the recording of the fluorescent image with time delay in relation to the generating radiation pulse so as to identify only the fluorescent response of the substance to be identified.

The disadvantages of this method include its invasiveness caused by the need for introducing exogenous fluorophore, as well as the complexity, high cost and relatively low resolution of the equipment required for producing the image with a millimicrosecond time delay in relation to the pulse of the radiation which induces fluorescence.

A known method of the diagnostics of affected tissues (Mechanisms of ratio fluorescence imaging of diseased tissue, Jianan Qu, Calum MacAulay, Stephen Lam and Branko Palcic, SPIE Proc. Vol. 2387, pp. 71–79), is the irradiation of the tissue segment under examination inducing endogenous fluorophores fluorescence with the wave length of 442 nm and the recording of two fluorescent images of the same tissue segment at the wave lengths of 500 nm and 630 nm. Then the ratio between two fluorescent images produced in the red and in the green wave length bands is taken, and the degree of effect on the tissue is determined by this ratio, if it exceeds a certain value.

The disadvantage of this method is relatively low sensitivity which dictates the need for using expensive cameras which brightness amplifiers. This is caused first of all by the fact that the blue radiation (442 nm) penetrates the tissue to quite insignificant depth and, respectively, can induce the fluorescence of only the fluorophores located close to the surface. Thus, it is difficult to carry out the diagnostics of defects under the surface. The optical properties of biological tissues in the blue (442 nm), green (500 nm) and red (630 nm) spectral bands are different to a significant extent and can vary from one patient to another which results in the need for using special algorithms for processing diagnostic information. Besides, railcar with the wave length of 442 nm falls into the band which induces the fluorescence of a whole range of endogenous fluorophores, such as collagen, elastin, porphyrins and their complexes with proteins, etc. Also, the concentration of porphyrins and their fluorescing complexes with proteins is frequently significantly lower than the concentration of other fluorophores. The fluorescence bands of various endogenous fluorophores are quite broad and partially overlap, therefore it is difficult to differentiate between them in case of their simultaneous excitation. Fluorescence of the fluorophores the concentration and distribution of which in tissues do not provide the required information regarding tissue condition is a confusing noise factor which distorts the informative signal.

A known method of detecting skin anomalies (Method of detecting anomalies of the skin, more particularly melanomae, and apparatus for carrying out the method, Gerhard Martens, Erhard P. H. Gunzel, U.S. Pat. No. 5,363,854, Nov. 15, 1994) is as follows: a skin segment under examination is irradiated in the ultraviolet spectrum band; the fluorescent image is recorded, and then the same skin segment is exposed to visible light, and the reference image of the same skin segment is recorded as seen in the visible band. Then a third image is produced where the brightness of each point is equal to the ratio between the brightness values of the first two images in the corresponding points. Skin segment anomalies are determined by brightness distribution in the third image.

The disadvantage of this method is its low sensitivity caused by the fact that wide band ultraviolet radiation induces the fluorescence of virtually all the fluorophores existing in the tissue under examination. It is possible to single out the fluorescent signal of one type of fluorophores which contains diagnostic information is possible only if the concentration of the fluorophores in question significantly exceeds that of other fluorophores. In a general case, this in turn is possible only in case of artificial invasive increase in their concentration. Apart from that, extremely low depth of penetration of ultraviolet radiation into skin tissue can be noted.

INVENTION DISCLOSURE

Technical Task

The proposed invention is aimed at increasing the precision, reliability and sensitivity of the diagnostics of proliferation areas in tissues in vivo, increasing the speed of diagnostics and eliminating the need for invasive intervention into the patient's organism.

Addressing the Technical Task

The indicated technical tasks are addressed as follows:
the tissue segment is evenly exposed to monochromatic radiation within the wave length band of 630 to 645 nm during the first period, and the fluorescent image of the tissue segment under examination is recorded in the spectral wave length band of 650 to 730 nm; the choice of the duration of the exposure and, respectively, the recording of the fluorescent image is based on the fluorescent signal intensity level and the dynamic range of the recording device; if the fluorescent signal intensity level equals the photon noise level or the internal noise of the recording device, recording is carried out in several cycles where the duration of each of them is determined with regard to the dynamic range value of the recording device, and the number of the cycles and, respectively, the total duration of the recording is determined on the basis of the required degree of statistical averaging of noise. The resulting fluorescent image is produced by way of averaging the brightness values of the corresponding points of the image for all recording cycles, determining the significant range of the brightness values of the averaged image and broadening this range by way of recalculation with regard to the entire dynamic range of the information display device.

The tissue segment under examination is evenly exposed to white light during the second period, and its reference colour image is recorded with the same angle and scale as in the case of recording the fluorescent image.

The areas where proliferation intensity changes in the tissue segments under examination are determined by formal signs in the fluorescent image, and the localisation areas are determined by comparing the fluorescent image with the reference colour image with the use of the coordinate grid, reference points applied thereon or by way of overlaying the images.

Besides, two auxiliary fluorescent images are recorded additionally during a diagnostic session with the use of the same equipment, in the same spectral band, with the same scale, wave length, density, power and duration of the exposure of the radiation inducing fluorescence as in the case of recording the fluorescent image of the tissue under examination.

The first auxiliary fluorescent image, the fluorescent image of the test object which is, for example, a cassette with several compartments filled with a stable fluorophore solution with known concentrations which differ by a known number of times from one compartment to another; the fluorophore solution should have the spectral bands of excitation and fluorescence which are similar to those of the endoporphyrins to be identified and their fluorescing protein complexes in the tissues under examination, and have the absorption and scattering values in the spectral bands under consideration which are similar to the corresponding values of the tissues under examination.

The first auxiliary fluorescent image is used to monitor (check) the diagnostic process sensitivity for ensuring its authenticity throughout the service life of the diagnostic equipment. Besides, by comparing the brightness values of particular segments in the fluorescent image of the tissue under examination and the first auxiliary fluorescent image (with the test object), the concentration of endogenous porphyrins and their fluorescing complexes with proteins in the tissue under examination is estimated.

The second auxiliary fluorescent image is the fluorescent image of the natural proliferation area of the same patient (for example, the growth areas of an unaffected nail plate).

The second auxiliary fluorescent image is used to determine contrast between the segments which correspond to actively proliferating tissue and are adjacent to poorly proliferating or non-proliferating tissue, as well as the brightness gradient between them. A similar procedure is applied to the fluorescent image of the tissue under examination, and the comparison is carried out between the contrast and brightness gradient at the second auxiliary fluorescent image. The degree of proliferation of the tissue under examination is estimated on the basis of the comparison results. The brightness values which are averaged for the recording period, as well as the brightness values averaged by the space which corresponds to the tissue segments in question are used for establishing contrast and brightness gradient in the fluorescent images.

Two more auxiliary monochrome images of the tissue under examination are recorded additionally with the same angle and scale as in the case of recording the fluorescent image to study the tissues that contain segments with (significantly) different absorption and scattering values in the spectrum bands used: one image (or the third auxiliary image) is recorded at the wave length of the used source of the radiation inducing fluorescence with even exposure of the tissue under examination to radiation from this source; another image (or the fourth auxiliary image) is recorded in the same spectral band where the fluorescent image is recorded, but with even exposure of the tissue under examination to radiation from an additional source in the same spectral band (in the fluorescence band used).

A coordinate grid and reference points are also applied to the third and fourth monochrome auxiliary images, or provisions are made for the possibility of overlaying or combining with the fluorescent and colour reference images of the tissue under examination.

The third and fourth monochrome auxiliary images are used to assess optical absorption and scattering values of the tissue segment under examination in the spectral bands that correspond to the selected bands of excitation and fluorescence of endogenous porphyrins and their fluorescing complexes with proteins. The location of local changes in optical absorption and scattering values is determined by comparing the third and fourth monochrome auxiliary images with the fluorescent and colour reference images of tissue under examination with the use of the coordinate grid or reference points applied thereon or by overlaying them on each other.

In order to implement the claimed method, a proliferation area diagnostics device is proposed; the layout of the device is displayed at FIG. 1; the device comprises a monochrome source of the radiation inducing the fluorescence of endogenous porphyrins and their complexes with proteins 3, fluorescence image recording unit 13, reference image recording unit 10, a computer with graphic data printing, documenting and storage devices 14, 15, 16. The distinctive feature of this device is that the monochrome source of the railcar inducing the fluorescence of endogenous porphyrins and their complexes with proteins operates within the wave length band of 630–645 nm, the fluorescent image recording unit is implemented in the form of a monochrome CCD-camera with variable frame exposure time and comprises additionally a white light source for exposing the tissue surface under examination when recording the reference colour image 1, a source of monochrome radiation within the wave length band of 650 to 730 nm for exposing the tissue under examination when recording the fourth monochrome auxiliary image 2, a source of lighting the laboratory premises in the visible spectrum band which does not radiate in the wave length band of above 650 nm 4, a radiation switching unit for sources 1, 2, 3 and a unit for making a collinear ray configuration 5, a unit of the collinear illumination of the tissue under examination from sources 1, 2, 3 and receiving reflected signals and the fluorescent signal 6, image splitting unit 11, radiation filtration unit 12, a processor for video signals, synchronisation and control signals 9 linked to a computer, the fluorescent image recording unit, the reference image recording unit, the unit for switching radiation sources and making a collinear ray configuration, the radiation filtration unit and radiation sources 1, 2, 3, 4.

The proposed device operates as follows

Radiation coming from source 3 through switching unit 5 and collinear illumination and receiving unit 6 evenly illuminates the tissue segment of object 7 under examination. The fluorescent response from the tissue segment of object 7 under examination is processed through collinear illumination and receiving unit 6 by lens 8 to be made an image at the receiving element of recording unit 13 through image splitting unit 11 and radiation filtration unit 12. The recording mode is input by the processor for video, synchronisation and control signals 9. The video signal comes from recording unit 13 to processor 9 which processes the recorded fluorescent image and transmits it to computer 14 and further to data printing and storage devices 15 and 16.

During the next period radiation coming from white light source 1 through switching unit 5 and collinear lighting and receiving unit 6 evenly illuminates the tissue segment of object 7 under examination. The light reflected from the tissue segment of object 7 under examination is processed through collinear illumination and receiving unit 6 by lens 8 to be made an image at the receiving element of recording unit 10 through image splitting unit 11. The recording mode is input by video, synchronisation and control signal processor 9. The video signal comes from recording unit 10 to processor 9 where the recorded reference image in colour is processed, if necessary, and is transmitted to computer 14 and further to data printing and storage devices 15 and 16.

The third auxiliary monochrome image is recorded with even illumination of the tissue segment of object 7 under examination by radiation from source 3 through switching unit 5 and collinear illumination and receiving unit 6. The light reflected from the tissue segment of object 7 under examination is processed through collinear illumination and receiving unit 6 by lens 8 to be made an image at the receiving element of recording unit 10 through image splitting unit 11 (or at recording unit 13 through image splitting unit 11 and radiation filtration unit 12; the filter is changed in this case upon a signal from processor 9). The recording mode is input by video, synchronisation and control signal processor 9. The video signal goes from recording unit 10 (or 13) to processor 9 where the recorded auxiliary image is processed, if necessary, and transmitted to computer 14 and further to data printing and storage devices 15 and 16.

The fourth auxiliary monochrome image is recorded with even illumination of the tissue segment of object 7 by radiation from source 2, through switching unit 5 and collinear illumination and receiving unit 6. The light reflected from the tissue segment of object 7 under examination is processed through collinear illumination and receiving unit 6 by lens 8 to be made an image at the receiving element of recording unit 10 through image splitting unit 11 (or at recording unit 13 through image splitting unit 11 and radiation filtration unit 12; the filter is changed in this case upon a signal from processor 9). The recording mode is input by video, synchronisation and control signal processor 9. The video signal goes from recording unit 10 (or 13) to processor 9 where the recorded auxiliary image is processed, if necessary, and transmitted to computer 14 and further to data printing and storage devices 15 and 16.

The first and second auxiliary fluorescent images are recorded in the same way as the fluorescent image of the tissue under examination (but with other recording objects).

The object position should not change when recording the fluorescent, colour reference, third and fourth auxiliary monochrome images.

The sequence of recording the fluorescent, colour reference, third and fourth auxiliary monochrome, first and second auxiliary fluorescent images can be different.

When looking for particular tissue segments (especially in case of endoscopic examination) the device operates in the view mode with continuous display of the colour and (or) fluorescent tissue image on the monitor screen.

The software of video, synchronisation and control signal processor 9 and computer 14 should support the operation of the claimed device with the use of the claimed method.

Positive Effect as Compared with Previous Technology Level

The aforementioned technical tasks are resolved by the proposed method due to the fact that, as compared with its analogues described above, firstly, in order to induce fluorescence, it uses long wave radiation in the wave length band of 630–645 nm which is within the fluorescence excitation band of only endogenous porphyrins and their complexes with proteins and does not induce interfering fluorescence of other endogenous fluorophores. However, it is known that it is the relative distribution of the concentration of endogenous porphyrins and their complexes with proteins in tissue that can provide information regarding the degree of proliferation of this or another tissue segment. Statistical processing of low level fluorescent signal allows to increase the real sensitivity of recording by averaging noise, since, according to classical statistics, the root-mean-square deviation of the number of independent events $\overline{\Delta n}$ is in proportion to the square root of the number of events n, the relative value of fluctuations is in inverse proportionality to; $\sqrt{n}$:

$$\Delta n/n \sim 1/\sqrt{n}$$

All this allows to record the fluorescent images reflecting the relative distribution of the natural concentrations of endogenous porphyrins and their complexes with proteins particularly in tissue and eliminates the need for preliminary preparation of the patient, as well as the need for invasive intervention into the patient's organism, increases the precision and reliability of diagnostics. Besides, it eliminates the need for using expensive recording equipment with cooled receivers, brightness intensifiers etc. The diagnostic information can be easily documented and interpreted.

The use of the colour reference image of the tissue under examination combined with the fluorescent image allows to precisely locate proliferation areas and makes the method more convenient in practical use.

The use of the first auxiliary fluorescent image of the test object allows to monitor the process of diagnostics and achieve the consistency of recording results, monitor porphyrin exchange fluctuations in tissues and proliferal activity fluctuations in the patient's organism over a long period of time.

The use of the second auxiliary fluorescent image allows to compare the degree of proliferation in the tissue under examination and the degree of proliferation in the healthy tissue of the same patient in the natural proliferation area. This allows to eliminate the effect of porphyrin exchange fluctuation factors on the results of diagnostics and the level of proliferative activity in the organism of a particular patient, that is, it allows to link the results of diagnostics to peculiarities in the organism of a particular patient.

The use of the third and fourth auxiliary images of the tissue under consideration allows to adjust the effect of local changes in optical absorption and scattering values of the tissue under examination in the spectral bands concerned on the fluorescent signal which increases the reliability of diagnostics.

The use of visible spectrum band without radiation in the wave length band of over 650 nm in the laboratory premises lighting source (FIG. 1) eliminates the need for working in complete darkness for the staff, since the laboratory premises should be fullly isolated from daylight (same as from other sources of interfering radiation in the wave length band which coincides with that in which fluorescent images are recorded).

INVENTION IMPLEMENTATION VERSIONS

Figure 1:
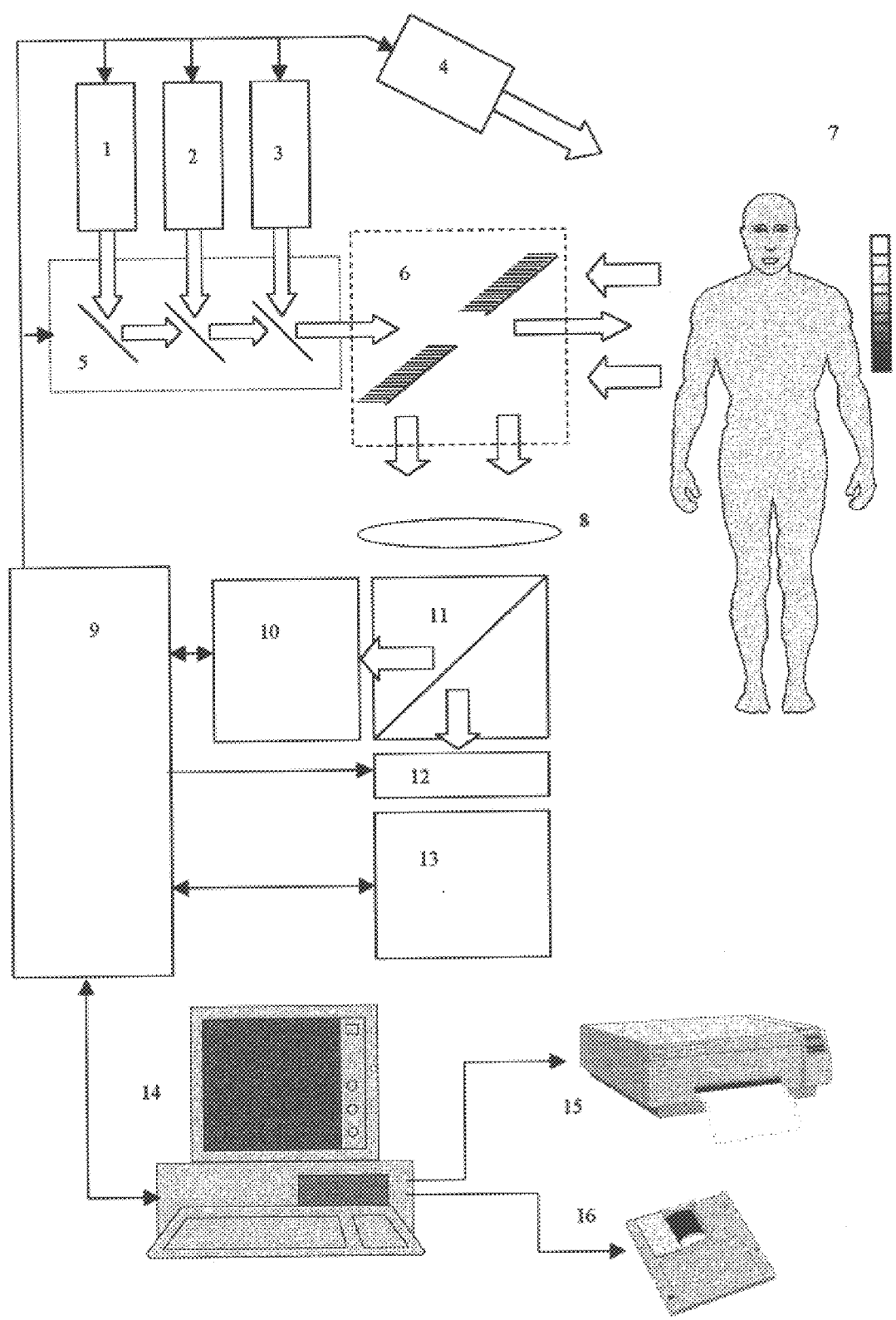
FIG. 1 displays the block diagram of proliferation area diagnostics device:
 1—white light source for illuminating the surface of tissue under examination when recording the colour reference image;
 2—source of monochrome radiation in the wave length band of 650–730 nm for illuminating the tissue under examination when recording the fourth monochrome auxiliary image;
 3—source of monochrome radiation inducing the fluorescence of endogenous porphyrins and their complexes with proteins in the wave length band of 630–645 nm;
 4—source of laboratory premises lighting in the visible spectrum band without radiation in the wave length band of above 650 nm;
 5—switching unit for radiation of sources 1, 2, 3 and making a collinear ray configuration;
 6—a unit for collinear illumination of tissue under examination from sources 1, 2, 3 and receiving reflected signals and the fluorescent signal;
 7—the object under examination and text object;
 8—lens;
 9—video, synchronisation and control signal processor;
 10—colour reference image recording unit;
 11—image splitting unit;
 12—radiation filtration unit;
 13—a unit for recording fluorescent images and auxiliary monochrome images (auxiliary monochrome images can also be recorded with the use of unit 10);
 14—a computer with graphical information display device;
 15—graphical data output and documenting device;
 16—data storage device FIG. 2 displays the fluorescent image of the finger of a healthy person. Intensive fluorescence areas correspond to nail plate growth area, a natural intensive proliferation area.

The white light source for illuminating tissue surface under examination when recording colour reference image 1 (FIG. 1) can be of any kind (including a pulse source) with the colour temperature required for normal colour reproduction of object 7 with colour reference image recording unit 10. Source 1 should provide for the possibility of control by turning on/off and (or) cutting off radiation at the output with the use of a shutter and, if necessary, colour adjustment by a control signal from video, synchronisation and control signal processor 9. The possibility of colour adjustment for the radiation of source 1 within a broad spectrum band will allow to carry out additional monitoring of various tissue defects by colour index with the use of the device. Source 1 should provide for even illumination intensity of the object within the field of view at the level required for normal operation of colour reference image recording unit 10.

The source of monochrome radiation in the wave length band of 650–730 nm for illuminating the tissue under examination when recording the fourth monochrome auxiliary image 2 (FIG. 1) can be implemented, for example, in the form of a semiconductor laser or laser block with the corresponding radiation wave length and a lens beam generation system. Source 2 should be controlled by a control signal from video, synchronisation and control signal processor 9 and should provide for even illumination intensity of the object within the field of view at the level required for normal operation of recording unit 13 (or recording unit 10).

Source of monochrome radiation inducing the fluorescence of endogenous porphyrins and their complexes with proteins 3 (FIG. 1) can be made, for example, in the form of a He-Ne laser ($\lambda$=632,8 nm) or a semiconductor laser (or laser block) with the length wave within the band of 630 to 645 nm. Source 3 should have a system of filtration of radiation with the wave length which exceeds 650 nm. The illumination intensity at the object within the field of view of the recording device operating in the wave length band of over 650 nm (that is, in the spectral sensitivity band of fluorescent image recording unit 13 determined by radiation filtration unit (12) supported by source 3 should be by approximately one order of magnitude lower that the fluorescent emittance level in the selected band of fluorescence of the patient's intact tissue with low proliferation degree. Source 3 should be controlled by a control signal coming from processor 9 and ensure even illumination intensity of the object located within the field of view of the device at the level of >~0,1 mWt/cm$^2$ (in continuous operation mode). It is possible to use a pulse source synchronised with recording unit 13 with the use of the synchronisation signals coming from processor The main requirement demanded of laboratory premises lighting source 4 (FIG. 1) is that the illumination intensity supported at the object located within the field of view of the recording device in the wave length band of over 650 nm should be approximately by one order of magnitude lower than the level of fluorescent emittance in the selected band of fluorescence of the patient's intact tissue with low proliferation degree. It is also desirable to make provisions for shading the area under examination and the optical elements of the device from radiation coming from source 4. Source 4 should support the illumination intensity in the laboratory premises which is sufficient for comfortable work of the staff. Source 4 should be controlled by a control signal coming from processor 9. It is possible to provide the operation mode of source 4 where the source would be switched off when fluorescent images are recorded by a signal coming from processor 9, or where its radiation would be cut off by a controlled light shutter.

Unit for switching the radiation of sources 1, 2, 3 and making a collinear ray configuration 5 (FIG. 1) can be made, for example, in the form of three controlled mirrors each of which can enter the operating position and direct radiation from the corresponding source along the optical axis of the device upon a control signal coming from processor 9. It is also possible to provide for a collinear configuration of rays coming from radiation sources 1, 2, 3 with the use of fibre optical directional couplers. In the case of making a device version for easily accessible surface proliferation areas (for example, on the skin), a shadow-free non-collinear illumination configuration can be used for illuminating the tissue segment under examination with the radiation coming from sources 1, 2, 3.

Unit for collinear illumination from sources 1, 2, 3 of tissue under examination and receiving reflected signals and fluorescent signal 6 (FIG. 1) can be made in the form of a mirror located at an angle to the optical axis of the device with a hole in the middle for letting through radiation from sources 1, 2, 3 illuminating the object. The signal reflected from the object and the fluorescent signal should be directed by the mirror to lens 8. Unit 6 can also comprise an optical system for generating a radiation spot from sources 1,2, 3. In the case of making a device version for endocscopic diagnostics, unit 6 should comprise an endoscopic channel matching optical system.

Lens 8 (FIG. 1) should have the maximum transmission in the spectral wave length band of 650 to 730 nm, the maximum aperture ratio and the back operating segment sufficient for accommodating image splitting unit 11 and radiation filtration unit 12. The lens resolution should be not lower than that of the receiving matrices of recording units 10 and 13.

Video, synchronisation and control signal processor 9 (FIG. 1) should have a broad dynamic range for digitising the images coming from the recording units, support the processing of the produced images in accordance with the claimed method, ensure consistent operation of all device units by generating the corresponding control and synchronisation signals according to an input algorithm and support bi-directional data exchange with computer 14. The software of video, synchronisation and control signal processor 9 and computer 14 should support the operation of the claimed device with the use of the claimed method.

Colour reference image recording unit 10 (FIG. 10) can be made in the form of a colour CCD-camera operating both in the continuous (view mode) and frame mode. The operation of the unit is controlled and synchronised with the use of the signals coming from processor 9.

Image splitting unit 11 (FIG. 1) can be a beam splitter in the form of a light splitting box with the splitting ratio of ≈1: 10, with the smaller portion being directed to colour reference image unit 10, or a thin-pellicular (0.5 mcm) beam splitter without a coating located at the angle of 45° to the optical axis and the splitting ratio of≈8:92 (pellicle beam splitter). if recording units 10 and 13 operate at different times, it is possible to use a controlled 100% mirror with two operating conditions.

Radiation filtration unit 12 (FIG. 1) can be made in the form of an absorption cut-off light filter as the simplest version; the transmission limits of this filter will be between the radiation wave length of source 3 and the spectral band centre of the produced endogenous porphyrin fluorescent response. The discrimination for the indicated wave lengths should be $\geq 10^5$. For the device version where the third auxiliary monochrome image is recorded with recording unit 13, this filter should be changed with a different filter which transmits radiation coming from source 3 upon a control signal coming from processor 9. In order to broaden the functional capabilities, radiation filtration unit 12 can contain a range of various band and cut-off light filters changed automatically upon a control signal coming from processor 9.

Fluorescent image and auxiliary monochrome image recording unit 13 (FIG. 1) can be made in the form of a monochrome CCD camera with adjustable frame exposure time. The operation of the unit is controlled and synchronised with the use of the signals coming from processor 9. The number of the elements and the size of the receiving matrices of recording units 13 and 10 should be matched. If source 3 operates in the pulse mode, recording unit 13 can additionally comprise a strobed electro-optial transducer with a photocathode with sensitivity in the wave length band of 650 to 730 nm.

Computer with graphical information display device 14 (FIG. 1), graphical information output and documenting device 15 and data storage device 16 should support high quality display, documenting and storage of the produced diagnostics information. The software of video, synchronisation and control signal processor 9 and computer 14 should support the operation of the claimed device with the use of the claimed method.

COMMERCIAL APPLICABILITY

Figure 5:
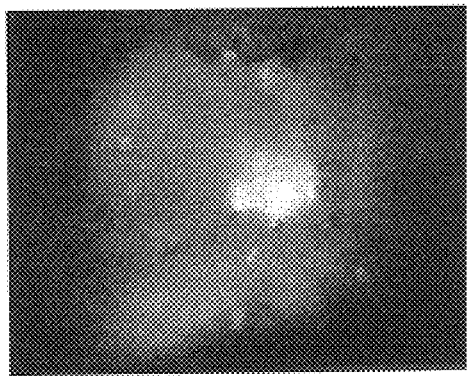
FIG. 5 displays the fluorescent image of a tumour area of patient T., 60 years of age. A continued tumour growth focus (1.7×1.5 cm) which cannot be identified visually is identified against the background of a slowly granulating wound developed as a result of malignant skin tumour dissection (metatypical cancer with the dimensions of 5×6 cm). The data was confirmed by a morphologic study of the operation material produced in a repeated operation. The wound surface in the fluorescent image corresponds to the light-grey background (feebly marked fluorescence of slowly developing granulations). There is a segment with more express fluorescence in the bottom right wound quadrant; this segment fully corresponds to continued tumour growth area.
Figure 6:
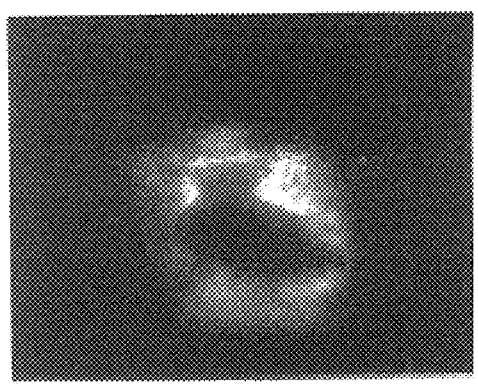
FIG. 6 displays the fluorescent image of the tumour area of patient C., 57 years of age. The diagnosis is back skin solid structure basalioma. The fluorescent image displays a bright area of active tumour proliferation which infiltrates the surrounding skin in peripheral areas outside visually identifiable limits.
Figure 7:
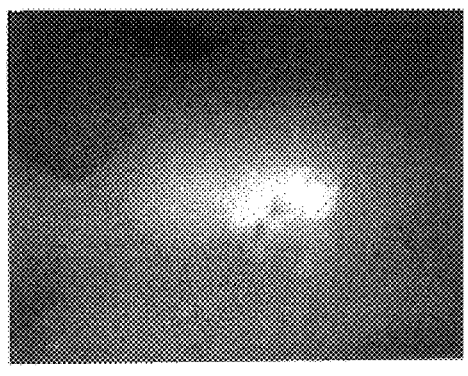
FIG. 7 displays the fluorescent image of the tumour area of patient M., 66 years of age. The diagnosis is disintegrating right palm skin syringoepitelioma. Intensive fluorescence areas correspond to active tumour proliferation areas. Dark spots in the tumour centre correspond to necrosis segments.

The device can be used first of all in ontological diagnostics as a method and tool for visualising the tumour growth areas that are frequently cannot be identified visually (see FIG. 5–7). The diagnostics is carried out with the use of non-invasive and contact-free techniques which require no preliminary preparation of the patient. 104 patients staying at the N.A. Semashko Central Clinical Hospital No. 4 of the Russian Federation Railway Ministry for examination and treatment of malignant tumours have been examined with the use of the model of the claimed device and the claimed method at the time of the application. The examination allowed in many cases to adjust the scope of the treatment, in particular, surgical intervention.

Figure 4:
FIG. 4 displays the fluorescent image of a healing wound on a patient's hand. Intensive fluorescence areas correspond to tissue reparation area.

Besides, the proposed method and device can be used in surgery as a means of monitoring post-operative tissue cicatrisation (see FIG. 4).

Figure 2:
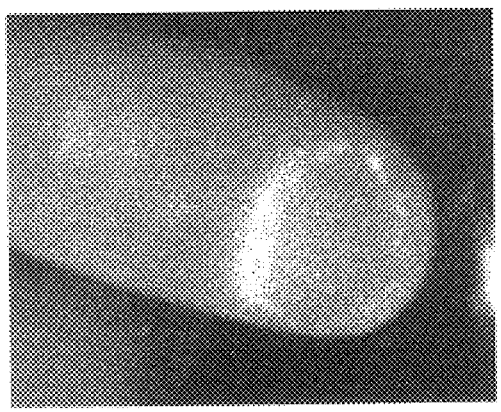
Figure 3:
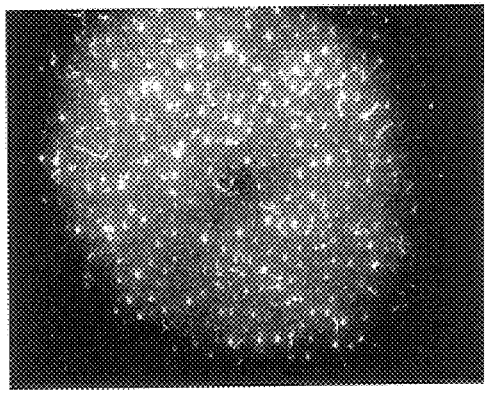
FIG. 3 displays the fluorescent image of a patient's back skin. The point foci of intensive fluorescence correspond to sebaceous gland location.

The proposed method and device can also be used in cosmetology and dermatology as a means of monitoring the condition of sebaceous glands (see FIG. 3), nail growth (see FIG. 2), etc.

What is claimed is:

1. Proliferation area diagnostics method the essence of which is in radiating tissue surface under examination with the radiation inducing the internal fluorescence of endogenous porphyrins and their complexes with proteins and recording the fluorescence of endogenous porphyrins and their complexes with proteins the distinctive feature of which is that the tissue segment under examination is irradiated with an even monochrome radiation beam in the wave length band of 630 to 645 nm, the fluorescent image of the tissue segment under examination is recorded only in the spectral wave band of 650 to 730 nm, and proliferation intensity change areas are determined by formal signs in the fluorescent image.

2. Method as indicated in claim 1, the distinctive feature of which is that the duration of exposure and recording the fluorescent image is chosen on the basis of the fluorescent signal intensity level, recording is carried out in one or several cycles the duration of each of which is determined on the basis of the dynamic range of the recording device, and the number of cycles is determined on the basis of the required degree of statistical averaging of noise; the resulting fluorescent image is produced by averaging the brightness values of the corresponding image points produced in all recording cycles, establishing the significant brightness range of the averaged image and broadening this range by re-calculating with regard to the entire dynamic range of the information display device.

3. Method as indicated in claim 1, the distinctive feature of which is that the tissue segment under examination is illuminated with white light additionally, before or after recording the fluorescent image, with monochrome radiation source being switched off; the colour reference image of the tissue segment is recorded with the same angle and scale as in the case of recording the fluorescent image, and proliferation area localisation points are established by comparing the fluorescent image with the colour reference image with the use of the coordinate grid and reference points applied to the images or by overlaying the images.

4. Method as indicated in claim 1, the distinctive feature of which is that the first auxiliary fluorescent image, the fluorescent image of the test object, is recorded additionally with the use of the same equipment, in the same spectral band, in the same scale and for the same wave length, density, power of and exposure to radiation inducing fluorescence as in the case of recording the fluorescent image of the tissue under examination, the test object being a cassette containing several compartments filled with a stable fluorophore solution with known concentrations which differ by a known number of times from one compartment to another; the fluorophore solution should have the spectral bands of excitation and fluorescence which are similar to those of the endoporphyrins and their fluorescing protein complexes to be identified in the tissues under examination, and have the absorption and scattering values in the spectral bands under consideration which are similar to the corresponding values of the tissues under examination. Then the brightness values of particular segments of fluorescent images of the tissue under examination and the first auxiliary fluorescent image are compared and the concentration of endogenous porphyrins and their fluorescing complexes with proteins in the tissue under examination is assessed.

5. Method as indicated in claim 1, the distinctive feature of which is that the second auxiliary fluorescent image, the fluorescent image of a natural proliferation area of the same patient, is recorded additionally, with establishing contrast between the segments corresponding to actively proliferating tissue and adjacent slightly proliferating or non-proliferating tissues, as well as the brightness gradient between them, comparing with contrast and brightness gradient at the fluorescent image of the tissue under examination; in order to determine contrast and brightness gradient in fluorescent images, the brightness values averaged during the recording period, as well as the brightness values averaged by the space corresponding to the tissue segments under examination are used, and the degree of proliferation of the tissue under examination is assessed with regard to the results of such comparison.

6. Method as indicated in claim 1, the distinctive feature of which that the third and fourth monochrome images of the tissue under examination are recorded with the same angle and scale as in the case of recording the fluorescent image; the third auxiliary image is recorded at the wave length of the source of radiation inducing fluorescence concerned with even illumination of the tissue under examination by the source, and the fourth auxiliary image is recorded in the spectral band in which the fluorescent image is recorded, but with even illumination of the tissue under examination with an additional source which operates in the same spectral band, and then the third and fourth monochrome auxiliary images are used to assess the optical absorption and scattering values of the tissue segment under examination in the spectral bands corresponding to the excitation and fluorescence bands of endogenous porphyrins and their fluorescing complexes with proteins concerned; local changes in optical absorption and scattering values are located by comparing the third and fourth monochrome auxiliary images a with the fluorescent and colour reference images of the tissue under examination with the use of a coordinate grid, reference points applied thereon or by overlaying them on each other.

7. A device for proliferation area diagnostics which comprises a monochrome source of the radiation inducing the fluorescence of endogenous porphyrins and their complexes with proteins, a fluorescent image recording unit, a reference image recording unit, a computer with graphical information display, output, documenting and storage devices the distinctive feature of which is that the monochrome source of radiation inducing the fluorescence of endogenous porphyrins and their complexes with proteins radiates in the wave length band of 630 to 645 nm, the fluorescent image recording unit is made in the form of a monochrome CCD-camera with variable frame exposure time and comprises additionally a white light source for illuminating the tissue surface under examination when recording colour reference image, a unit for switching radiation sources and making a collinear configuration of rays, a unit for collinear illumination of the tissue under examination and receiving reflected signals and the fluorescent signal, an image splitting unit, a radiation filtration unit, a video, synchronisation and control signal processor linked to a computer, the fluorescent image recording unit, the reference image recording unit, the unit for switching radiation from sources and making a collinear ray configuration, the radiation filtration unit and the radiation sources.

8. Device as indicated in claim 7, the distinctive feature of which is that it comprises additionally a source of monochrome radiation in the wave length band of 650 to 730 nm for illuminating the tissue under examination when recording the monochrome auxiliary image linked to the video, synchronisation and control signal processor.

9. Device as indicated in claim 7, the distinctive feature of which is that it comprises additionally a laboratory premises lighting source which operates in the visible spectrum band, does not radiate in the wave length band of over 650 nm and is linked to the video, synchronisation and control signal processor.

* * * * *